US010687913B2

(12) United States Patent
Kitamura et al.

(10) Patent No.: US 10,687,913 B2
(45) Date of Patent: Jun. 23, 2020

(54) IMAGE PROCESSING DEVICE, IMAGE PROCESSING METHOD, AND COMPUTER-READABLE RECORDING MEDIUM FOR DETECTING ABNORMALITY FROM INTRALUMINAL IMAGE USING INTEGRATED FEATURE DATA

(71) Applicant: OLYMPUS CORPORATION, Tokyo (JP)

(72) Inventors: Makoto Kitamura, Hachioji (JP); Toshiya Kamiyama, Hachioji (JP); Mitsutaka Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 163 days.

(21) Appl. No.: 15/705,657

(22) Filed: Sep. 15, 2017

(65) Prior Publication Data

US 2018/0014902 A1 Jan. 18, 2018

Related U.S. Application Data

(63) Continuation of application No. PCT/JP2015/058616, filed on Mar. 20, 2015.

(51) Int. Cl.
*A61B 90/00* (2016.01)
*A61B 1/045* (2006.01)
(Continued)

(52) U.S. Cl.
CPC ........ *A61B 90/361* (2016.02); *A61B 1/00009* (2013.01); *A61B 1/045* (2013.01);
(Continued)

(58) Field of Classification Search
None
See application file for complete search history.

(56) References Cited

U.S. PATENT DOCUMENTS 8,233,711 B2 7/2012 Wang et al.
2008/0279431 A1 11/2008 Kitamura
(Continued)

FOREIGN PATENT DOCUMENTS

| JP | 2008-278964 A | 11/2008 |
| JP | 2013-085718 A | 5/2013 |
| JP | 2013-111420 A | 6/2013 |

OTHER PUBLICATIONS

International Search Report dated Jun. 9, 2015 issued in PCT/JP2015/058616.

*Primary Examiner* — Tahmina N Ansari
(74) *Attorney, Agent, or Firm* — Scully, Scott, Murphy & Presser, P.C.

(57) ABSTRACT

An image processing device includes: an abnormality candidate region detection unit configured to detect, from an intraluminal image obtained by imaging a living body lumen, an abnormality candidate region in which a tissue characteristic of the living body or an in-vivo state satisfies a predetermined condition; a feature data calculation unit configured to calculate, from each of a plurality of regions inside the intraluminal image, a plurality of pieces of feature data including different kinds; an integrated feature data calculation unit configured to calculate integrated feature data by integrating the plurality of pieces of feature data based on information of the abnormality candidate region; and a detection unit configured to detect an abnormality from the intraluminal image by using the integrated feature data.

30 Claims, 8 Drawing Sheets

(51) Int. Cl.
  *A61B 1/00* (2006.01)
  *A61B 1/04* (2006.01)
(52) U.S. Cl.
  CPC ..... *A61B 1/041* (2013.01); *G06T 2207/10068* (2013.01); *G06T 2207/30096* (2013.01)

(56) References Cited

U.S. PATENT DOCUMENTS

| | | | |
|---|---|---|---|
| 2010/0183204 A1* | 7/2010 | Kanda | G06T 7/248 382/128 |
| 2013/0051642 A1* | 2/2013 | Kanda | G06T 7/0012 382/128 |
| 2013/0094726 A1* | 4/2013 | Kitamura | G06T 7/64 382/128 |
| 2014/0270377 A1* | 9/2014 | Kanda | A61B 1/00009 382/103 |
| 2018/0014902 A1* | 1/2018 | Kitamura | A61B 90/361 |

* cited by examiner

IMAGE PROCESSING DEVICE, IMAGE PROCESSING METHOD, AND COMPUTER-READABLE RECORDING MEDIUM FOR DETECTING ABNORMALITY FROM INTRALUMINAL IMAGE USING INTEGRATED FEATURE DATA

CROSS-REFERENCE TO RELATED APPLICATION

This application is a continuation of International Application No. PCT/JP2015/058616, filed on Mar. 20, 2015, the entire contents of which are incorporated herein by reference.

BACKGROUND

The present disclosure relates to an image processing device, an image processing method, and a computer-readable recording medium.

In the related art, disclosed is a method (bag of features: BoF) of calculating a plurality of pieces of local feature data from an image and performing highly accurate identification by using integrated feature data obtained by integrating the respective local feature data (refer to U.S. Pat. No. 8,233,711 B and Non-Patent Literature 1, for example). A procedure of this processing is as follows.

Step 1: Calculate local feature data from an image.

Step 2: Divide the image into rectangular regions of multiple sizes to create a pyramid image.

Step 3: Calculate a distance between local feature data in each rectangular region and a representative vector group prepared in advance in a local feature space, find a representative vector located closest, and calculate a frequency distribution (integrated feature data) thereof.

Step 4: Determine normality or abnormality by comparing the frequency distribution calculated for each of the rectangular regions with normal and abnormal frequency distributions prepared in advance.

SUMMARY

An image processing device according to one aspect of the present disclosure may include: an abnormality candidate region detection unit configured to detect, from an intraluminal image obtained by imaging a living body lumen, an abnormality candidate region in which a tissue characteristic of the living body or an in-vivo state satisfies a predetermined condition; a feature data calculation unit configured to calculate, from each of a plurality of regions inside the intraluminal image, a plurality of pieces of feature data including different kinds; an integrated feature data calculation unit configured to calculate integrated feature data by integrating the plurality of pieces of feature data based on information of the abnormality candidate region; and a detection unit configured to detect an abnormality from the intraluminal image by using the integrated feature data.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following, modes to implement the present disclosure (hereinafter referred to as "embodiments") will be described.

First Embodiment

Figure 1:
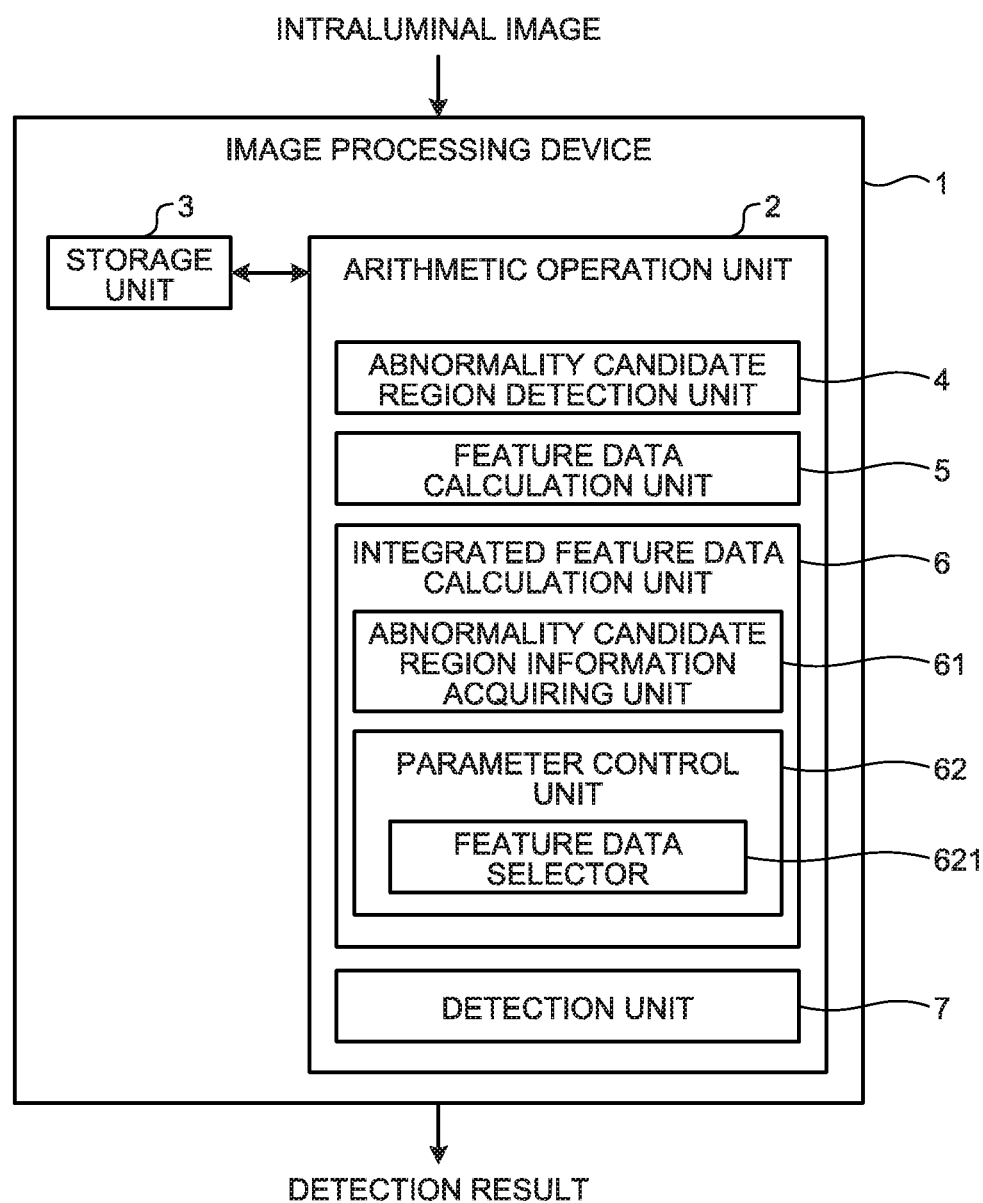
FIG. 1 is a block diagram illustrating a functional configuration of an image processing device according to a first embodiment of the present disclosure.

FIG. 1 is a block diagram illustrating a functional configuration of an image processing device according to a first embodiment of the present disclosure. An image processing device 1 illustrated in the drawing includes an arithmetic operation unit 2 and a storage unit 3. The image processing device 1 has a function to acquire an intraluminal image captured by a capsule endoscope, an endoscope, or the like, and perform predetermined image processing. As the intraluminal image, used is a color image having pixel levels (pixel values) relative to wavelength components of R (red), G (green), and B (blue) in each pixel position.

The arithmetic operation unit 2 includes an abnormality candidate region detection unit 4 adapted to detect, from an intraluminal image, an abnormality candidate region in which a tissue characteristic of a living body or an in-vivo state satisfies a predetermined condition; a feature data calculation unit 5 adapted to calculate, from each of a plurality of regions inside the intraluminal image, a plurality of pieces of feature data including different kinds; an integrated feature data calculation unit 6 adapted to calculate integrated feature data by integrating the plurality of pieces of feature data based on information of the abnormality candidate region; and a detection unit 7 adapted to detect an abnormality from the intraluminal image by using the integrated feature data.

The abnormality candidate region detection unit 4 detects, as an abnormality candidate region, a region in which a tissue characteristic of a living body or an in-vivo state in the intraluminal image satisfies the predetermined condition.

Examples of such an abnormality candidate region may include: a region where a tissue characteristic of a living body is changed, such as aphtha, an ulcer, erosion, a polyp, tumor, rubor, or chorionic abnormality; and a region where a state is changed inside the living body, such as bleeding. Such an abnormality candidate region may also be referred to as a region where a lesion is occurring. Note that the abnormality candidate region may be a part of an image or an entire part of the image.

The abnormality candidate region detection unit 4 detects an abnormality candidate region from an intraluminal image based on color feature data, shape feature data and/or texture feature data. For example, since aphtha, an ulcer, or the like indicate a specific color of white, and bleeding or rubor indicate a specific color of red, detection based on the color feature data is possible. Additionally, since a polyp or tumor often has a circular region, detection based on the shape feature data is possible. Furthermore, since chorionic abnormality or the like often has non-uniform patterns on a mucosal surface, detection based on the texture feature data is possible. The abnormality candidate region detection unit 4 detects the mentioned abnormality candidate regions based on the color feature data, shape feature data, and/or texture feature data.

First, a description will be provided for a case where the abnormality candidate region detection unit 4 extracts an abnormality candidate region based on color feature data. In this case, the abnormality candidate region detection unit 4 determines whether each pixel is an abnormality candidate region based on color feature data of each pixel to be processed and the determination criterion. The determination criterion for the color feature data referred to by the abnormality candidate region detection unit 4 is determined and stored in the storage unit 3 based on color feature data including: pixel values of respective R, G, B components in a specific region collected in advance; a value secondarily calculated by a known conversion based thereon; a color difference (YCbCr conversion); a hue; saturation (HSI conversion); color ratio (G/R and B/G); and the like.

Meanwhile, while the method in which the abnormality candidate region detection unit 4 detects an abnormality candidate region based on the determination criterion prepared in advance has been described here, any method may be adopted as far as an abnormal color region may be detected from inside of an image. For example, the abnormality candidate region detection unit 4 may detect an abnormality candidate region by a method based on a feature space distance from representative color feature data. Additionally, instead of using color feature data of each pixel, the abnormality candidate region detection unit 4 may also detect an abnormality candidate region by using color feature data of each of small regions after dividing edge information or the like inside an image into the small regions.

Next, a description will be provided for a case where the abnormality candidate region detection unit 4 detects an abnormality candidate region based on shape feature data. In this case, the abnormality candidate region detection unit 4 calculates gradient intensity of each pixel (such as luminance value and G value) inside an image by the known Sobel, Laplacian, or the like, and calculates a correlation value between the gradient intensity and a circular model stored in the storage unit 3, and then detects, as an abnormality candidate region, a circular region where the correlation value is a predetermined threshold or more.

Meanwhile, while the method in which the abnormality candidate region detection unit 4 detects an abnormality candidate region by performing pattern matching with the circular model prepared in advance has been described here, but any method may be adopted as far as a circular region may be detected from an image, such as the known Hough transform, random sample consensus (RANSAC), a deformable part model (DPM), or an ellipse and line segment detector (ELSD).

Next, a description will be provided for a case where the abnormality candidate region detection unit 4 detects an abnormality candidate region based on texture feature data. In this case, the abnormality candidate region detection unit 4 determines whether each rectangular region is an abnormality candidate region based on texture feature data calculated for each of rectangular regions obtained by dividing an image into rectangles, and also based on the determination criterion stored in advance by the storage unit 3. The determination criterion for the texture feature data referred to by the abnormality candidate region detection unit 4 is determined based on texture feature data such as local binary pattern (LBP) feature data and variance of an RGB value in an abnormal region collected in advance.

Figure 2:
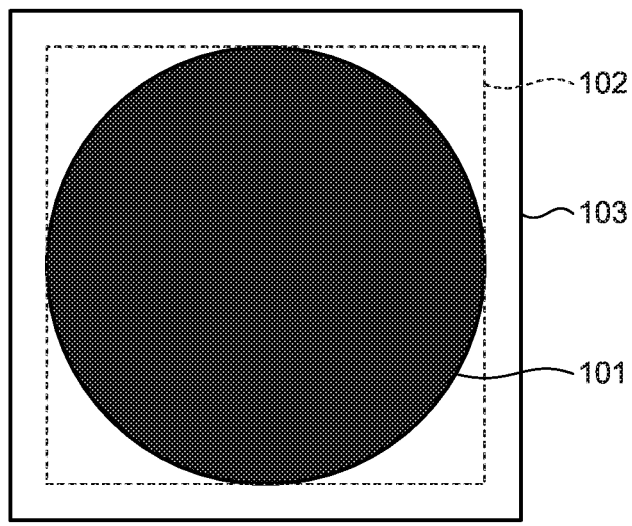
FIG. 2 is a diagram schematically illustrating an outline of processing applied to an abnormality candidate region by a feature data calculation unit of the image processing device according to the first embodiment of the present disclosure.

The feature data calculation unit 5 performs labeling processing for an abnormality candidate region, extracts a circumscribing rectangular region circumscribing each abnormality candidate region, and sets an extended region by deforming the circumscribing rectangular region. As for the extended region, an extended region is set by extending a circumscribing rectangular region n ($1.0 < n \leq 2.0$) times. A value of n in this case is set to n=1.0+(area of abnormality candidate region/maximum area variable) (1), for example, based on the area of the abnormality candidate region. The "maximum area variable" on a right side of the expression (1) represents the area serving as a reference in order to set a circumscribing rectangular region, and corresponds to a maximum value of the area assumed as an abnormality candidate region. FIG. 2 is a diagram schematically illustrating an outline of processing applied to an abnormality candidate region by the feature data calculation unit 5. FIG. 2 illustrates a case where a circumscribing rectangular region 102 is extracted relative to a circular abnormality candidate region 101 to set an extended region 103.

Figure 3:
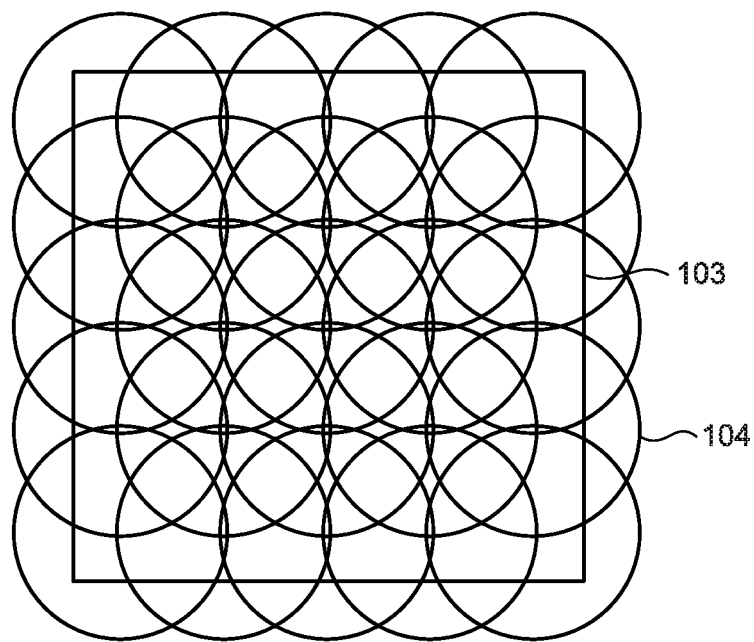
FIG. 3 is a diagram schematically illustrating an outline of processing in which the feature data calculation unit of the image processing device according to first embodiment of the present disclosure extracts a circular region.

The feature data calculation unit 5 extracts representative pixel positions at regular intervals or at random from the extended region, and extracts circular regions each having a predetermined radius centering each of the pixel positions. FIG. 3 is a diagram schematically illustrating an outline of the processing in which the feature data calculation unit 5 extracts circular regions. FIG. 3 illustrates a case where the feature data calculation unit 5 extracts a plurality of circular regions 104 centering respective pixel positions extracted at regular intervals relative to the extended region 103. As a method of thus extracting the circular regions, for example, a method called DENS may be applied. Meanwhile, as a method of extracting a circular region, scale-invariant feature transform (SIFT) to detect a key point (feature point) may also be used (refer to pages 5 to 22 of Computer Vision Saisentan Guide 2 by Adcom Media, Inc., for example).

The feature data calculation unit 5 calculates, as a plurality of kinds of feature data, color feature data (such as RGB average value, YCbCr average value, HSI average value, G/R average value, and B/G average value), shape feature data (such as histograms of oriented gradients (HoG) and SIFT), and texture feature data (such as LBP, variance, kurtosis, and skewness), and the like. Note that the kinds of feature data described here are merely examples and other kinds of feature data may also be used.

The integrated feature data calculation unit 6 includes: an abnormality candidate region information acquiring unit 61 adapted to acquire information of an abnormality candidate region; and a parameter control unit 62 adapted to control a calculation parameter for integrated feature data based on the information of the abnormality candidate region.

The abnormality candidate region information acquiring unit 61 determines an abnormality kind in an abnormality candidate region based on a detection result of the abnormality candidate region detection unit 4. Specifically, when detection is made by the abnormality candidate region detection unit 4, the abnormality candidate region information acquiring unit 61 determines that a region determined as an abnormality candidate region based on color feature data has a color abnormality, determines that a region determined as an abnormality candidate region based on shape feature data has a shape abnormality, and determines that a region determined as an abnormality candidate region based on texture feature data has a texture abnormality. Additionally, an abnormality kind may also be determined by the determination criterion prepared in advance based on feature data distributions such color feature data (such as RGB and HSV), shape information (such as HoG, area, a circumference length, and a Feret diameter), and texture feature data (such as LBP), calculated from respective abnormality kinds.

The parameter control unit 62 includes a feature data selector 621 adapted to set, as a calculation parameter, number of dimensions for each kind of feature data used to calculate integrated feature data, and select feature data in accordance with the number of dimensions set for each kind. When an abnormality kind in an abnormality candidate region is a color abnormality, the feature data selector 621 preferentially selects color feature data over other kinds of feature data, in the case of a shape abnormality, the feature data selector preferentially selects shape feature data over other kinds of feature data, and in the case of a texture abnormality, the feature data selector preferentially selects texture feature data over other kinds of feature data. In other words, when an abnormality kind in an abnormality candidate region is a color abnormality, the feature data selector 621 sets the number of dimensions for color feature data to become larger than the number of dimensions for other kinds of feature data, in the case of a shape abnormality, the feature data selector sets the number of dimensions for shape feature data to become larger than the number of dimensions for other kinds of feature data, and in the case of a texture abnormality, the feature data selector sets the number of dimensions for texture feature data to become larger than the number of dimensions for other kinds of feature data. In the following, examples of setting specific number of dimensions when there are three kinds of feature data (color feature data, shape feature data, texture feature data) and the number of dimensions for feature data to be selected is 100 dimensions will be described.

(1) Case of Color Abnormality
Color feature data: 80 dimensions, shape feature data: 10 dimensions, and texture feature data: 10 dimensions (2) Case of Shape Abnormality
Color feature data: 10 dimensions, shape feature data: 80 dimensions, texture feature data: 10 dimensions (3) Case of Texture Abnormality
Color feature data: 10 dimensions, shape feature data: 10 dimensions, texture feature data: 80 dimensions Note that selection ratios described here are merely examples, and in the case of, for example, (1) color abnormality, any setting may be possible as far as the number of dimensions for the color feature data is maximal.

The integrated feature data calculation unit 6 calculates, based on feature data selected by the feature data selector 621, integrated feature data having predetermined number of dimensions by using the above-described BoF, the known Fisher Vector, or the like. In the first embodiment, the number of dimensions for the integrated feature data is preset. When the integrated feature data calculation unit 6 calculates integrated feature data by using the BoF, the number of dimensions for the integrated feature data is equal to number of representative vectors. Additionally, when the integrated feature data calculation unit 6 calculates integrated feature data by using the Fisher Vector, the number of dimensions for the integrated feature data is equal to number of distributions.

Using the integrated feature data calculated by the integrated feature data calculation unit 6, the detection unit 7 detects an abnormal region by a classifier such as a known support vector machine (SVM) (as for the SVM, refer to pages 95 to 102 of Computer Vision Saisentan Guide 3 by Adcom Media, Inc., for example).

The arithmetic operation unit 2 is implemented by using a general-purpose processor such as a central processing unit (CPU) having arithmetic and control functions, a dedicated integrated circuit such as an application specific integrated circuit (ASIC) or a field programmable gate array (FPGA), or the like. When the arithmetic operation unit 2 is implemented by the general-purpose processor or the FPGA, various kinds of programs and various kinds of data stored in the storage unit 3 are read from the storage unit 3 to provide commands to the respective units constituting the image processing device 1, perform data transfer, and the like, thereby controlling operation of the entire image processing device 1. When the arithmetic operation unit 2 is implemented by using the ASIC, various kinds of processing may be individually executed, or various kinds of processing may also be executed by using various kinds of data and the like stored in the storage unit 3.

The storage unit 3 stores data of an intraluminal image to be processed; and various kinds of information necessary at the time of performing processing. The storage unit 3 is implemented by various kinds of IC memories such as a read only memory (ROM) or a random access memory (RAM), a hard disk built inside or connected by a data communication terminal, an information recording device such as a CD-ROM, a reading device thereof, and the like. The storage unit 3 stores not only image data of an intraluminal image acquired by the image processing device 1 but also a program to operate the image processing device 1 and also to cause the image processing device 1 to execute various functions, data to be used during execution of the program, and the like. Specifically, the storage unit 3 stores an image processing program according to the first embodiment and various kinds of parameters such as a threshold used at the time of performing the image processing.

The various kinds of programs such as an image processing program stored in the storage unit 3 may be recorded in a computer-readable recording medium. Additionally, the various kinds of programs may be recorded in the storage unit 3 or the recording medium when a computer or a recording medium is shipped as a product, or may be downloaded via a communication network. The communication network referred to here is implemented by, for example, an existing public line network, a local area network (LAN), a wide area network (WAN), and the like, and may be either one of wired and wireless.

The image processing device 1 having the above-described configuration may be implemented by using one computer or may be implemented by using a plurality of computers. In the latter case, processing may be performed in mutual cooperation while data is exchanged via a communication network. Meanwhile, the computer referred to here may be constituted by, for example, a general-purpose personal computer, a server, and the like.

Figure 4:
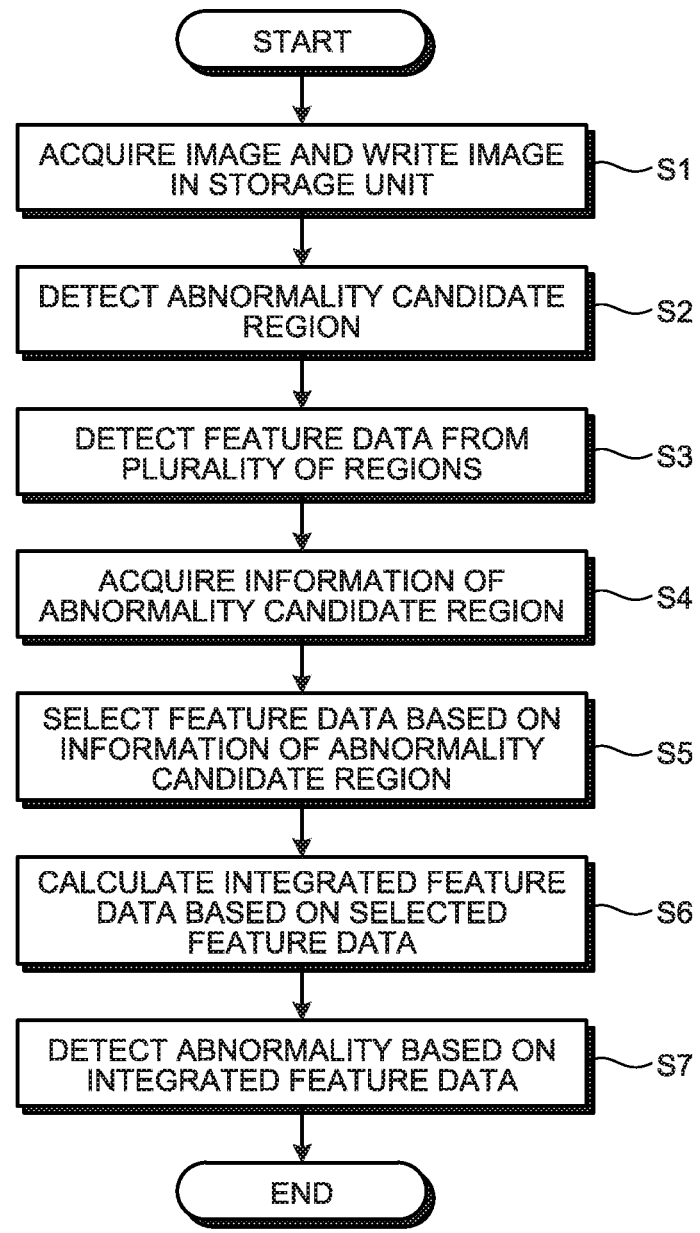
FIG. 4 is a flowchart illustrating an outline of processing executed by the image processing device according to the first embodiment of the present disclosure.

FIG. 4 is a flowchart illustrating an outline of processing executed by the image processing device 1. First, the image processing device 1 acquires an intraluminal image to be processed, writes and stores the same in the storage unit 3 (step S1). The image processing device 1 may acquire an intraluminal image by communicating with a device such as a capsule endoscope that captures the intraluminal image, or may acquire an intraluminal image by reading data thereof from a recording medium having the intraluminal image recorded.

Subsequently, the abnormality candidate region detection unit 4 detects an abnormality candidate region from the intraluminal image based on color feature data, shape feature data, and/or texture feature data (step S2).

After that, the feature data calculation unit 5 calculates a plurality of pieces of feature data including different kinds from each of the plurality of regions in the image (step S3). First, the feature data calculation unit 5 extracts a circumscribing rectangular region that circumscribes each abnormality candidate region, and sets an extended region by deforming the circumscribing rectangular region (refer to FIG. 2). Subsequently, the feature data calculation unit 5 extracts pixel positions at regular intervals or at random from the extended region. After that, the feature data calculation unit 5 extracts a plurality of circular regions centering the extracted pixel positions as a plurality of regions (refer to FIG. 3), and calculates a plurality of pieces of feature data for each of the circular regions. The plurality of pieces of feature data calculated by the feature data calculation unit 5 includes, for example, color feature data, shape feature data, texture feature data, and the like.

Subsequently, the abnormality candidate region information acquiring unit 61 acquires information of an abnormality candidate region as information to control a calculation parameter for integrated feature data (step S4). Specifically, the abnormality candidate region information acquiring unit 61 determines an abnormality kind in an abnormality candidate region based on a detection result of the abnormality candidate region detection unit 4.

After that, the feature data selector 621 selects feature data based on the information of the abnormality candidate region (step S5). At this point, the feature data selector 621 sets the number of dimensions for each kind of feature data in accordance with the number of dimensions set for each kind of feature data based on the information of the abnormality candidate region, and selects feature data of each kind in accordance with the number of dimensions.

Subsequently, the integrated feature data calculation unit 6 calculates integrated feature data by integrating a plurality of pieces of feature data based on the feature data selected by the feature data selector 621 (step S6).

Finally, the detection unit 7 detects an abnormality in the intraluminal image based on the calculated integrated feature data, and outputs a detection result (step S7).

According to the first embodiment of the present disclosure described above, since an abnormality candidate region is detected and a plurality of kinds of feature data is integrated based on the information of the detected abnormality candidate region, integrated feature data suitable for accurately representing an observation object may be appropriately acquired.

Additionally, according to the first embodiment, since feature data used to calculate integrated feature data is suitably selected in accordance with information of an abnormality candidate region, the integrated feature data according to the abnormality candidate region may be calculated, and erroneous detection and detection failure may be prevented.

Modified Example 1-1

A second example of abnormality candidate region information acquiring processing and feature data selecting processing performed by the abnormality candidate region information acquiring unit 61 will be described as a modified example 1-1 of the first embodiment. In the present modified example 1-1, the abnormality candidate region information acquiring unit 61 calculates clarity at a boundary of an abnormality candidate region.

First, the abnormality candidate region information acquiring unit 61 calculates a pixel average value (such as luminance average value, G average value, and G/R average value) in each abnormality candidate region.

Subsequently, the abnormality candidate region information acquiring unit 61 calculates a pixel average value (such as luminance average value, G average value, and G/R average value) of a region that is not an abnormality candidate region in each extended region.

Figure 5:
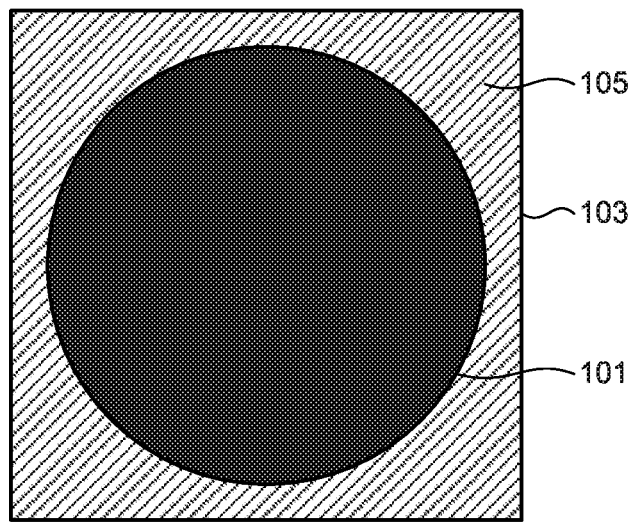
FIG. 5 is a diagram illustrating an example of an abnormality candidate region and a region that is not an abnormality candidate region inside an extended region.

After that, the abnormality candidate region information acquiring unit 61 calculates a difference between a pixel average value in each abnormality candidate region and a pixel average value in a region that is not an abnormality candidate region in the extended region. FIG. 5 is a diagram illustrating an example of an abnormality candidate region and a region that is not an abnormality candidate region inside an extended region. A region 105 illustrated in FIG. 5 indicates a region which is not the abnormality candidate region 101 inside the extended region 103.

Finally, when the difference between the pixel average values is a predetermined value or more, the abnormality candidate region information acquiring unit 61 determines that the boundary is clear, and when the difference between the average values of the pixel values is less than the predetermined value, the abnormality candidate region information acquiring unit determines that the boundary is unclear.

In the present modified example 1-1, the feature data selector 621 sets the number of dimensions for each feature data to be selected based on clarity at the boundary of the abnormality candidate region. Meanwhile, a case of having three kinds of feature data (color feature data, shape feature data, and texture feature data) is exemplified in the modified examples described below, but needless to mention, this is merely an example.

(1) Case where Boundary is Clear

This may be a probable case where a significant difference appears in a color and a shape between an abnormal region and a normal region. In this case, the feature data selector 621 preferentially selects color feature data and the shape feature data and sets the number of dimensions for the color feature data and shape feature data to become larger than the number of dimensions for the texture feature data. For example, when the number of dimensions for feature data to be selected is 100 dimensions, the feature data selector 621 sets the color feature data to 40 dimensions, the shape feature data to 40 dimensions, and the texture feature data to 20 dimensions.

(2) Case where Boundary is Unclear

This may be a probable a case where there is no significant difference in a color and a shape between an abnormal region and a normal region. In this case, the feature data selector 621 preferentially selects texture feature data, and sets the number of dimensions for the texture feature data to become larger than the number of dimensions number for color feature data and shape feature data. For example, when the number of dimensions for feature data to be selected is 100 dimensions, the feature data selector 621 sets the color feature data to 10 dimensions, the shape feature data to 10 dimensions, and the texture feature data to 80 dimensions.

Modified Example 1-2

A third example of the abnormality candidate region information acquiring processing and the feature data selecting processing performed by the abnormality candidate region information acquiring unit 61 will be described as a modified example 1-2 of the first embodiment. In the present modified example 1-2, the abnormality candidate region information acquiring unit 61 determines an organ kind in an intraluminal image. As for a determination method for an organ kind, used is a method of determining an organ kind based on average R, G, B values in an intraluminal image (refer to JP 2006-288612 A, for example). The storage unit 3 preliminarily stores numerical ranges of average values of R, G, and B in images of the stomach, small intestine, and large intestine. The abnormality candidate region information acquiring unit 61 compares R, G, B average values in an image with the numerical value ranges of the stomach, small intestine, and large intestine stored in the storage unit 3, thereby determining an organ kind.

In the present modified example 1-2, the feature data selector 621 sets the number of dimensions for each feature data to be selected based on the organ kind determined by the abnormality candidate region information acquiring unit 61.

(1) When Organ Kinds are Stomach and Small Intestine

This is a case where a main object to be detected has an abnormality having features in a color and texture, such as bleeding or erosion/ulcer. In this case, the feature data selector 621 preferentially selects color feature data and texture feature data, and sets the number of dimensions for the color feature data and the texture feature data to become larger than the number of dimensions for the shape feature data. For example, when the number of dimensions of feature data to be selected is 100 dimensions, the feature data selector 621 sets the color feature data to 40 dimensions, the shape feature data to 20 dimensions, and the texture feature data to 40 dimensions.

(2) When Organ Kind is Large Intestine

This is a case where a main object to be detected has an abnormality having a feature in a shape, such as a polyp or tumor. In this case, the feature data selector 621 preferentially selects shape feature data, and sets the number of dimensions for the shape feature data to become larger than the number of dimensions for color feature data and texture feature data. For example, when the number of dimensions of feature data to be selected is 100 dimensions, the feature data selector 621 sets the color feature data to 10 dimensions, the shape feature data to 80 dimensions, and the texture feature data to 10 dimensions.

Modified Example 1-3

A fourth example of the abnormality candidate region information acquiring processing and the feature data selecting processing performed by the abnormality candidate region information acquiring unit 61 will be described as a modified example 1-3 of the first embodiment. In the present modified example 1-3, the abnormality candidate region information acquiring unit 61 determines whether an abnormality candidate region exists in a bubble inner region. The storage unit 3 stores a bubble model prepared in advance from a bubble image.

First, the abnormality candidate region information acquiring unit 61 calculates gradient intensity from each pixel (luminance value, G value, and the like) in an image by the known Sobel, Laplacian, or the like.

Subsequently, the abnormality candidate region information acquiring unit 61 calculates a correlation value in each pixel position between a bubble model stored in the storage unit 3 and a gradient intensity image.

After that, the abnormality candidate region information acquiring unit 61 extracts, as a bubble inner region, a region where a correlation value with the bubble model is a predetermined threshold or more.

Subsequently, the abnormality candidate region information acquiring unit 61 calculates a gravity center position of each abnormality candidate region.

Figure 6:
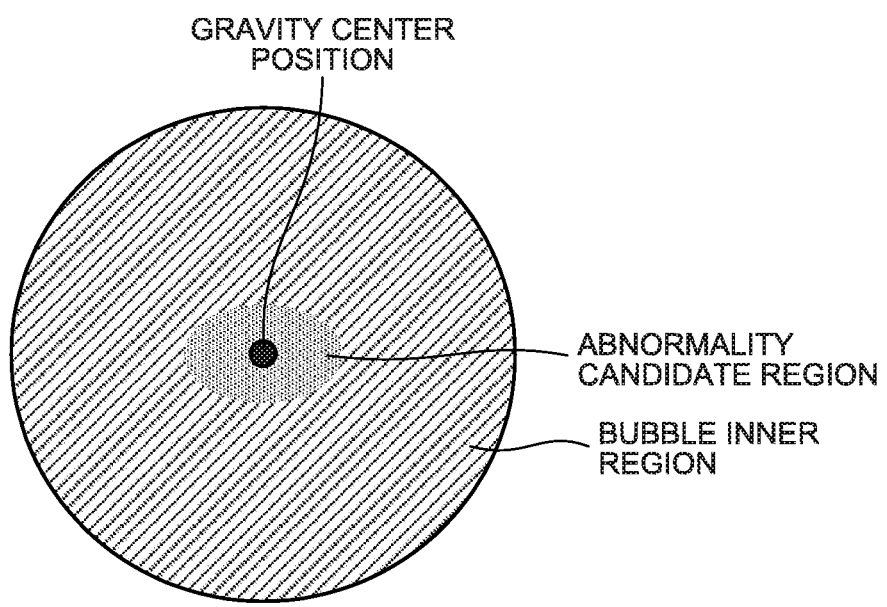
FIG. 6 is a diagram schematically illustrating a case where a gravity center position of an abnormality candidate region exists in a bubble inner region.

Finally, the abnormality candidate region information acquiring unit 61 determines whether the gravity center position of the abnormality candidate region exists in the bubble inner region or a bubble outer region. FIG. 6 is a diagram schematically illustrating a case where the gravity center position of the abnormality candidate region exists in the bubble inner region. In the case illustrated in FIG. 6, the abnormality candidate region information acquiring unit 61 determines that the gravity center position exists in the bubble inner region.

In the present modified example 1-3, when the abnormality candidate region exists in the bubble inner region, the feature data selector 621 sets the number of dimensions for each feature data to be selected. When the abnormality candidate region exists in the bubble inner region, redness in a mucosal region becomes stronger, and therefore, it may be considered that there is no significant difference in color between an abnormal region and a normal region. In this case, the feature data selector 621 preferentially selects shape feature data and texture feature data, and sets the number of dimensions for the shape feature data and the texture feature data to become larger than the number of dimensions for color feature data. For example, when the number of dimensions for the feature data to be selected is 100 dimensions, the feature data selector 621 sets the color feature data to 20 dimensions, the shape feature data to 40 dimensions, and the texture feature data to 40 dimensions.

When it is determined that an abnormality candidate region exists in the bubble outer region, the feature data selector 621 sets the number of dimensions for the three kinds of feature data substantially uniform. For example, when the number of dimensions for feature data to be selected is 100 dimensions, the feature data selector 621 sets the number of dimensions for two kinds out of the three kinds to 33 dimensions, and sets the number of dimensions for the remaining one kind to 34 dimensions. Additionally, a prescribed balance determined in advance, which is not uniform, may also be set.

Modified Example 1-4

A fifth example of the abnormality candidate region information acquiring processing and the feature data selecting processing performed by the abnormality candidate region information acquiring unit 61 will be described as a modified example 1-4 of the first embodiment. In the present modified example 1-4, the abnormality candidate region information acquiring unit 61 determines whether an abnormality candidate region exists in a dark region.

First, the abnormality candidate region information acquiring unit 61 calculates a luminance average value (such as G average value) in each extended region.

After that, when a luminance average value is a predetermined threshold value or less, the abnormality candidate region information acquiring unit 61 determines that an abnormality candidate region exists in the dark region.

In the present modified example 1-4, when it is determined that the abnormality candidate region exists in the dark region, the feature data selector 621 sets the number of dimensions for each feature data to be selected. When the abnormality candidate region exists in the dark region, it may be considered that there is no significant difference in color between an abnormal region and a normal region. In this case, the feature data selector 621 preferentially selects shape feature data and texture feature data, and sets the number of dimensions for the shape feature data and the texture feature data to become larger than the number of dimensions for color feature data. For example, when the number of dimensions for the feature data to be selected is 100 dimensions, the feature data selector 621 sets the color feature data to 20 dimensions, the shape feature data to 40 dimensions, and the texture feature data to 40 dimensions.

When it is determined that an abnormality candidate region exists in a bright region, the feature data selector 621 sets the number of dimensions for the three kinds of feature data substantially uniform. For example, when the number of dimensions for feature data to be selected is 100 dimensions, the feature data selector 621 sets the number of dimensions for two kinds out of the three kinds to 33 dimensions, and sets the number of dimensions for the remaining one kind to 34 dimensions.

Modified Example 1-5

A sixth example of the abnormality candidate region information acquiring processing and the feature data selecting processing performed by the abnormality candidate region information acquiring unit 61 will be described as a modified example 1-5 of the first embodiment. In the present modified example 1-5, the abnormality candidate region information acquiring unit 61 determines whether an abnormality candidate region exists in a halation region.

First, the abnormality candidate region information acquiring unit 61 calculates a luminance average value (such as G average value) in each extended region.

After that, when a luminance average value is a predetermined threshold or more, the abnormality candidate region information acquiring unit 61 determines that the abnormality candidate region exists in the halation region.

In the present modified example 1-5, when it is determined that the abnormality candidate region exists in the halation region, the feature data selector 621 sets the number of dimensions for each feature data to be selected. When the abnormality candidate region exists in the halation region, it is considered that color balance is lost. In this case, the feature data selector 621 preferentially selects shape feature data and texture feature data, and sets the number of dimensions for the shape feature data and the texture feature data to become larger than the number of dimensions for color feature data. For example, when the number of dimensions for the feature data to be selected is 100 dimensions, the feature data selector 621 sets the color feature data to 20 dimensions, the shape feature data to 40 dimensions, and the texture feature data to 40 dimensions.

When it is determined that the abnormality candidate region exists in a non-halation region, the feature data selector 621 sets the number of dimensions for the three kinds of feature data substantially uniform. For example, when the number of dimensions for feature data to be selected is 100 dimensions, the feature data selector 621 sets the number of dimensions for two kinds out of the three kinds to 33 dimensions, and sets the number of dimensions for the remaining one kind to 34 dimensions.

Modified Example 1-6

A seventh example of the abnormality candidate region information acquiring processing and the feature data selecting processing performed by the abnormality candidate region information acquiring unit 61 will be described as a modified example 1-6 of the first embodiment. In the present modified example 1-6, the abnormality candidate region information acquiring unit 61 calculates a mucosal color in an image. The storage unit 3 stores a determination criterion (color range) for a mucosal region determined based on color feature data such as pixel values of respective R, G, B components in a mucosal region and a non-mucosal region collected in advance, values secondarily calculated by known conversion based thereon, a color difference (YCbCr conversion), a color phase, saturation (HSI conversion), and a color ratio (G/R and B/G).

The abnormality candidate region information acquiring unit 61 determines whether each pixel exists in a mucosal region based on the color feature data of each pixel to be processed and also based on the determination criterion for the mucosal region stored in the storage unit 3.

Subsequently, the abnormality candidate region information acquiring unit 61 calculates color feature data (G/R average value) of a mucosal region.

Finally, when the color feature data (G/R average value) is less than a predetermined threshold, the abnormality candidate region information acquiring unit 61 determines that the region is a mucosal region having a mucosal color with strong redness, and when the G/R average value is the predetermined threshold or more, the abnormality candidate region information acquiring unit determines that the region is a mucosal region having a mucosal color with weak redness.

In the present modified example 1-6, the feature data selector 621 sets the number of dimensions for each feature data to be selected based on redness intensity of a mucosal color in an image.

(1) When Mucosal Color has Strong Redness

This may be a probable case where there is no significant difference in color between an abnormal region and a normal region. In this case, the feature data selector 621 preferentially selects shape feature data and texture feature data, and sets the number of dimensions for the shape feature data and the texture feature data to become larger than the number of dimensions for color feature data. For example, when the number of dimensions for the feature data to be selected is 100 dimensions, the feature data selector 621 sets the color feature data to 20 dimensions, the shape feature data to 40 dimensions, and the texture feature data to 40 dimensions.

(2) When Mucosal Color has Weak Redness

This may be a probable case where a significant difference appears in color between an abnormal region and a normal region. In this case, the feature data selector 621 preferentially selects color feature data, and sets the number of dimensions for the color feature data to become larger than the number of dimensions for shape feature data and texture feature data. For example, when the number of dimensions for the feature data to be selected is 100 dimensions, the feature data selector 621 sets the color feature data to 80 dimensions, the shape feature data to 10 dimensions, and the texture feature data to 10 dimensions.

Needless to mention that the above-described modified examples 1-1 to 1-6 bring the effects similar to those of the first embodiment.

Note that the processing of the feature data selector 621 described in the modified examples 1-1 to 1-6 may be suitably combined with the processing of the feature data selector 621 described in first embodiment. For example, in the case of selecting various kinds of feature data by suitably combining selection methods of the first embodiment and the modified examples 1-1 to 1-6, an average of the number of dimensions respectively set for the various kinds of feature data may be a final setting value. Specifically, in the case of combining, for example, two selection methods, the number of dimensions for the various kinds of feature data set by one selection method are as follows: color feature data: 80 dimensions, shape feature data: 10 dimensions, texture feature data: 10 dimensions, and the number of dimensions for the various kinds of feature data set by the other selection method are as follows: color feature data: 10 dimensions, shape feature data: 80 dimensions, texture feature data: 10 dimensions. In this case, the feature data selector 621 calculates an average of the number of dimensions for the various kinds of feature data, thereby setting the final number of dimensions for the color feature data to 45 dimensions, the shape feature data to 45 dimensions, and the texture feature data to 10 dimensions.

Furthermore, priority order may also be preset for a plurality of selection methods. In this case, the number of dimensions for each feature data may be set by adding a predetermined weight in accordance with the priority order.

Additionally, the image processing device 1 may be provided with a function as an input unit adapted to receive a command signal such that a user may provide a command for a selection method via the input unit. Here, the input unit may be implemented by using a user interface such as a keyboard, a mouse, or the like. Meanwhile, when the image processing device 1 includes a display unit, a touch panel may be provided on a display panel surface such that the touch panel may be made to function as an input unit.

Second Embodiment

Figure 7:
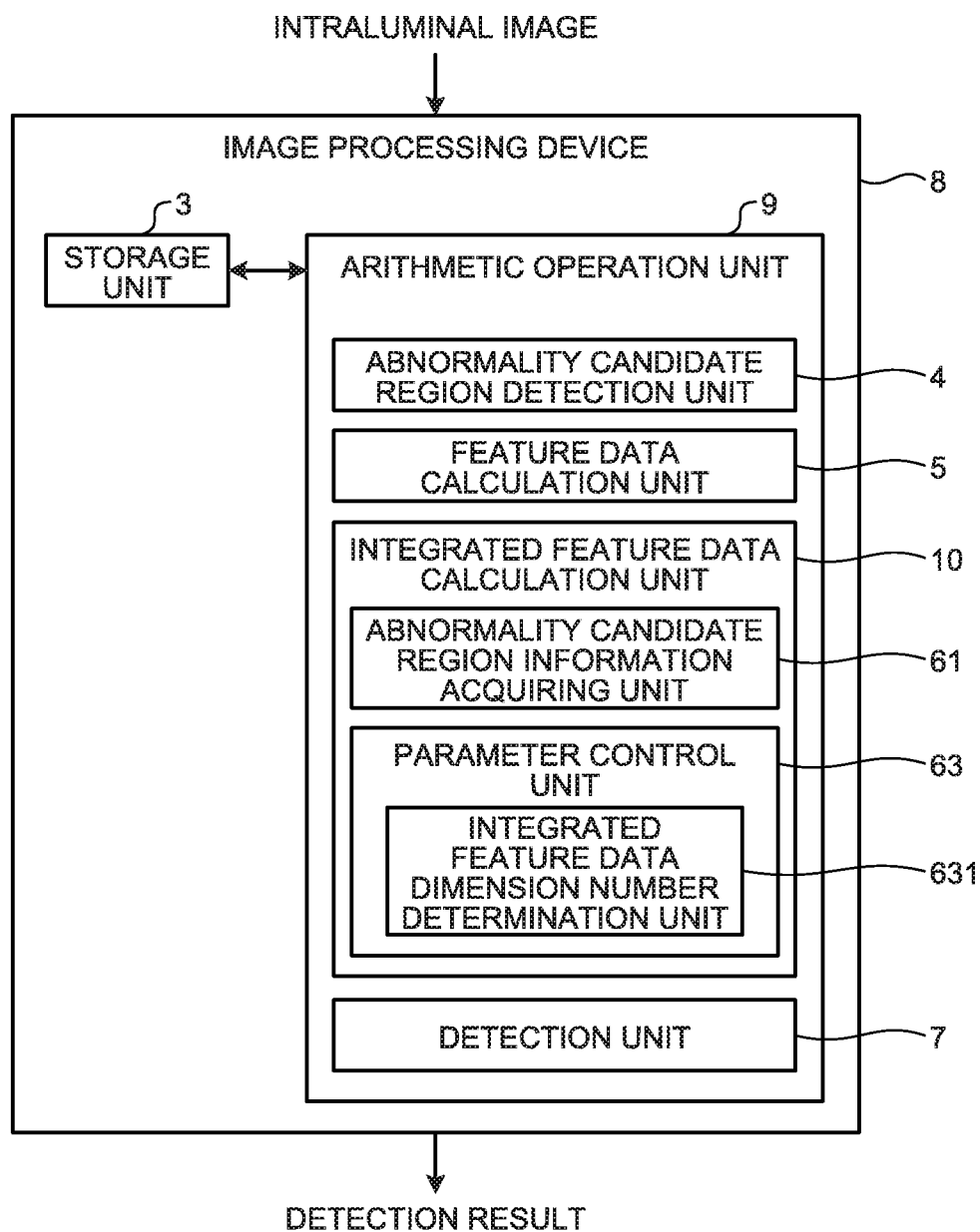
FIG. 7 is a block diagram illustrating a functional configuration of an image processing device according to a second embodiment of the present disclosure.

FIG. 7 is a block diagram illustrating a functional configuration of an image processing device according to a second embodiment of the present disclosure. An image processing device 8 illustrated in the drawing includes an arithmetic operation unit 9 and a storage unit 3. In the following, a description will be provided while a component similar to a component of an arithmetic operation unit 2 in an image processing device 1 according to a first embodiment is denoted by a same reference sign.

The arithmetic operation unit 9 includes an abnormality candidate region detection unit 4, a feature data calculation unit 5, an integrated feature data calculation unit 10, and a detection unit 7. The integrated feature data calculation unit 10 includes an abnormality candidate region information acquiring unit 61 and a parameter control unit 63.

The parameter control unit 63 includes an integrated feature data dimension number determination unit 631 adapted to determine, as a calculation parameter, the number of dimensions for integrated feature data based on an abnormality kind in an abnormality candidate region. Specifically, when an abnormality kind is a color abnormality, the integrated feature data dimension number determination unit 631 sets the number of dimensions for integrated feature data to become smaller than that in the a case where an abnormality kind is a shape abnormality or a texture abnormality. This is because, when the abnormality kind is the color abnormality, it may be considered that a significant difference appears between an abnormal region and a normal region.

In the case of using the BoF, for example, the integrated feature data calculation unit 10 sets number of representative vectors as the number of dimensions for integrated feature data, and in the case of using the Fisher Vector, the integrated feature data calculation unit calculates integrated feature data while using number of distributions as the number of dimensions for the integrated feature data.

Figure 8:
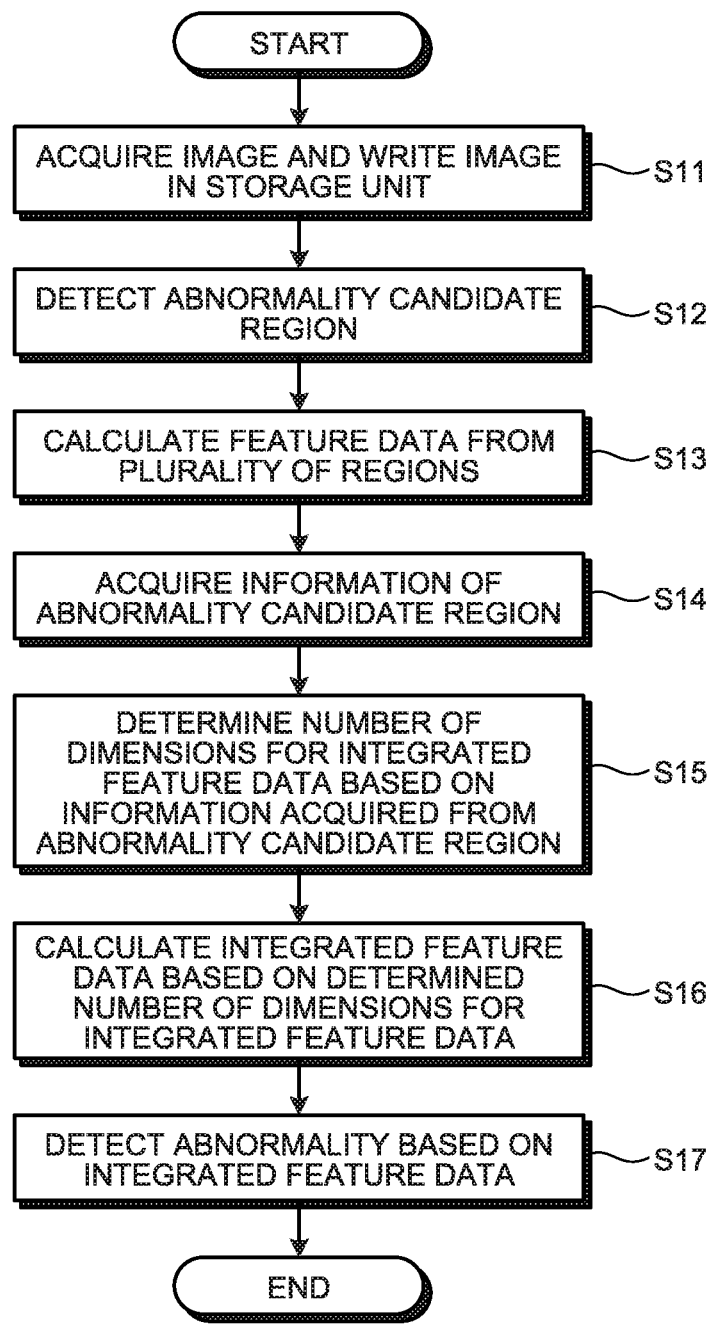
FIG. 8 is a flowchart illustrating an outline of processing executed by the image processing device according to the second embodiment of the present disclosure.

FIG. 8 is a flowchart illustrating an outline of processing performed by the image processing device 8. Processing in steps S11 to S14 and S17 is similar to processing in steps S1 to S4 and S7 in FIG. 4, respectively.

In step S15, the integrated feature data dimension number determination unit 631 determines the number of dimensions for integrated feature data based on information acquired from an abnormality candidate (step S15).

After that, the integrated feature data calculation unit 10 calculates integrated feature data based on the number of dimensions for the integrated feature data determined by the integrated feature data dimension number determination unit 631 (step S16).

After the detection unit 7 detects an abnormality in step S17, the image processing device 8 finishes a series of the processing.

According to the second embodiment of the present disclosure described above, since an abnormality candidate region is detected and a plurality of kinds of feature data is integrated based on information of the detected abnormality candidate region, the integrated feature data suitable for accurately representing an observation object may be appropriately acquired in a manner similar to the first embodiment.

Additionally, according to the second embodiment, since the number of dimensions for the integrated feature data is suitably determined in accordance with the information of the abnormality candidate region, the integrated feature data according to the abnormality candidate region may be calculated, and erroneous detection and detection failure may be suppressed.

Modified Example 2-1

A second example of integrated feature data dimension number determination processing performed by the integrated feature data dimension number determination unit 631 will be described as a modified example 2-1 of the present embodiment. The integrated feature data dimension number determination unit 631 determines the number of dimensions for integrated feature data based on clarity at a boundary of an abnormality candidate region. Specifically, when a boundary is clear, the integrated feature data dimension number determination unit 631 sets the number of dimensions for integrated feature data to become smaller than that when the boundary is unclear. This is because, when the boundary is clear, it may be considered that a significant difference appears between an abnormal region and a normal region.

Modified Example 2-2

A third example of the integrated feature data dimension number determination processing performed by the integrated feature data dimension number determination unit 631 will be described as a modified example 2-2 of the present embodiment. The integrated feature data dimension number determination unit 631 determines the number of dimensions for integrated feature data based on an organ kind in an intraluminal image in which an abnormality candidate region is captured. Specifically, the integrated feature data dimension number determination unit 631 sets the number of dimensions for integrated feature data of an organ to be examined to become larger than the number of dimensions for integrated feature data of an organ not to be examined. Consequently, the organ to be examined may be accurately detected.

Modified Example 2-3

A fourth example of the integrated feature data dimension number determination processing performed by the integrated feature data dimension number determination unit 631 will be described as a modified example 2-3 of the present embodiment. The integrated feature data dimension number determination unit 631 determines the number of dimensions for integrated feature data based on whether an abnormality candidate region exists in a bubble inner region. Specifically, when the abnormality candidate region exists in the bubble inner region, the integrated feature data dimension number determination unit 631 sets the number of dimensions for integrated feature data to become larger than that in the case of existing in a bubble outer region. This is because, when the abnormality candidate region exists in the bubble inner region, a mucosal region has strong redness, and it may be considered that a significant difference hardly appears between an abnormal region and a normal region.

Modified Example 2-4

A fifth example of the integrated feature data dimension number determination processing performed by the integrated feature data dimension number determination unit 631 will be described as a modified example 2-4 of the present embodiment. The integrated feature data dimension number determination unit 631 determines the number of dimensions for integrated feature data based on whether an abnormality candidate region exists in a dark region. Specifically, when the abnormality candidate region exists in the dark region, the integrated feature data dimension number determination unit 631 sets the number of dimensions for integrated feature data to become larger than that in the case of existing in a non-dark region. This is because, when the abnormality candidate region exists in the dark region, it may be considered that a significant difference hardly appears between an abnormal region and a normal region.

Modified Example 2-5

A sixth example of the integrated feature data dimension number determination processing performed by the integrated feature data dimension number determination unit 631 will be described as a modified example 2-5 of the present embodiment. The integrated feature data dimension number determination unit 631 determines the number of dimensions for integrated feature data based on whether an abnormality candidate region exists in a halation region. Specifically, when the abnormality candidate region exists in the halation region, the integrated feature data dimension number determination unit 631 sets the number of dimensions for integrated feature data to become larger than that when of existing in a non-halation region. This is because, when the abnormality candidate region exists in the halation region, it may be considered that a significant difference hardly appears between an abnormal region and a normal region.

Modified Example 2-6

A seventh example of the integrated feature data dimension number determination processing performed by the integrated feature data dimension number determination unit 631 will be described as a modified example 2-6 of the present embodiment. The integrated feature data dimension number determination unit 631 determines the number of dimensions for integrated feature data based on a mucosal color in an intraluminal image. Specifically, when the mucosal color has strong redness, the integrated feature data dimension number determination unit 631 sets the number of dimensions for integrated feature data to become larger than that when the mucosal color has weak redness. This is because, when the mucosal color has strong redness, it may be considered that a significant difference hardly appears between an abnormal region and a normal region.

Needless to mention, the modified examples 2-1 to 2-6 described above bring effects similar to those of the above-described second embodiment.

Note that the processing of the integrated feature data dimension number determination unit 631 described in the modified examples 2-1 to 2-6 may be suitably combined with the processing of the integrated feature data dimension number determination unit 631 described in the second embodiment. For example, an average of the number of dimensions determined in respective integrated feature data dimension number determination processing may be determined as the number of dimensions for integrated feature data. Additionally, priority order may be preset for a plurality of integrated feature data dimension number determination processing to be combined, and it may be possible to finally determine, as the number of dimensions for integrated feature data, the number of dimensions for integrated feature data obtained by adding, to the number of dimensions determined by each integrated feature data dimension number determination processing, a weight in accordance with the priority order.

Third Embodiment

Figure 9:
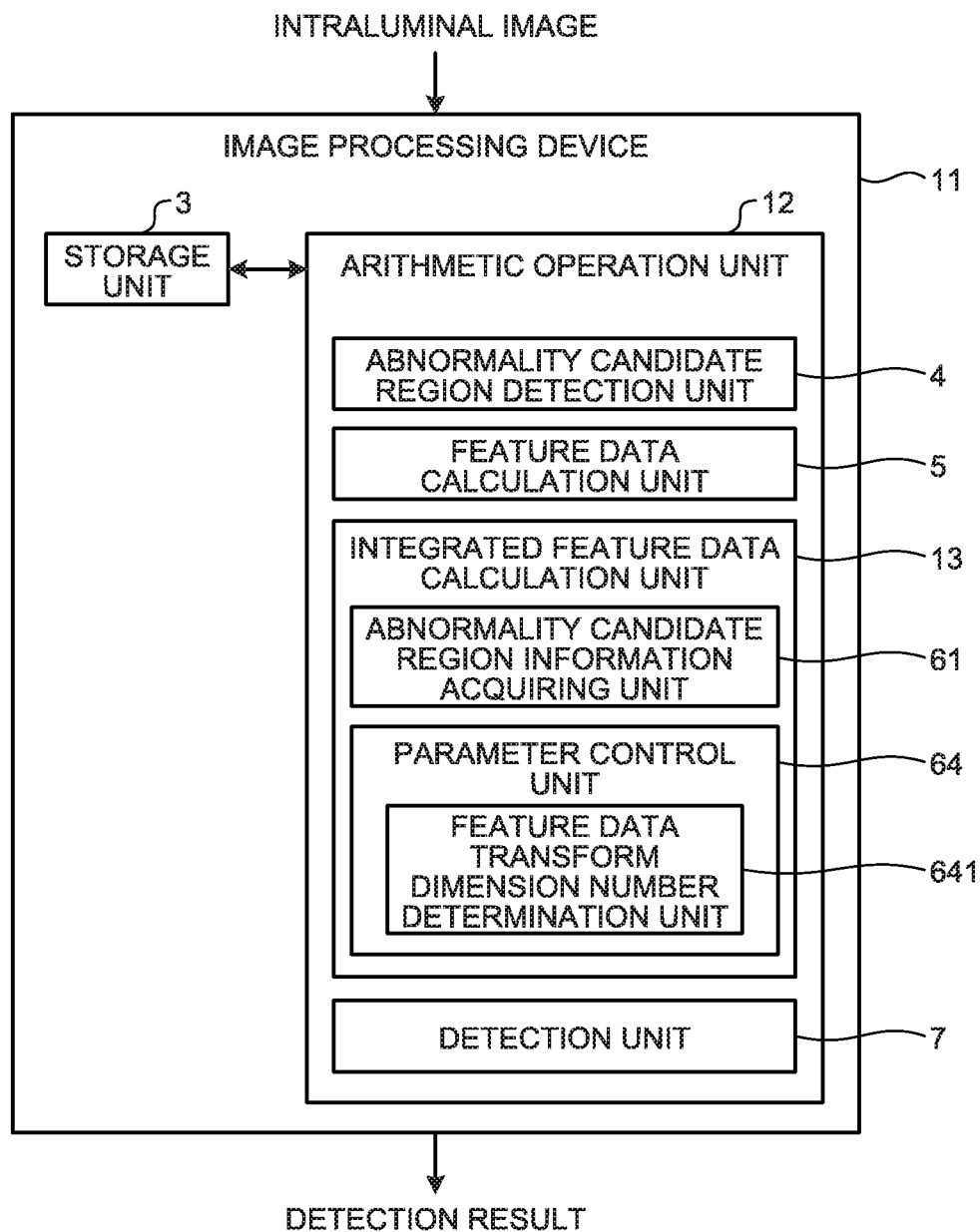
FIG. 9 is a block diagram illustrating a functional configuration of an image processing device according to a third embodiment of the present disclosure.

FIG. 9 is a block diagram illustrating a functional configuration of an image processing device according to a third embodiment of the present disclosure. An image processing device 11 illustrated in the drawing includes an arithmetic operation unit 12 and a storage unit 3. In the following, a description will be provided while a component similar to a component of an arithmetic operation unit 2 in an image processing device 1 according to a first embodiment is denoted by a same reference sign.

The arithmetic operation unit 12 includes an abnormality candidate region detection unit 4, a feature data calculation unit 5, an integrated feature data calculation unit 13, and a detection unit 7. The integrated feature data calculation unit 13 includes an abnormality candidate region information acquiring unit 61 and a parameter control unit 64.

The parameter control unit 64 includes a feature data transform dimension number determination unit 641 adapted to determine transform number of dimensions for feature data based on information of an abnormality candidate region. Specifically, when a kind of an abnormality candidate region is a color abnormality, the feature data transform dimension number determination unit 641 sets the transform number of dimensions to become smaller than that when a kind of an abnormality candidate region is a shape abnormality or a texture abnormality. This is because, when the abnormality kind is the color abnormality, it may be considered that a significant difference appears between an abnormal region and a normal region.

Figure 10:
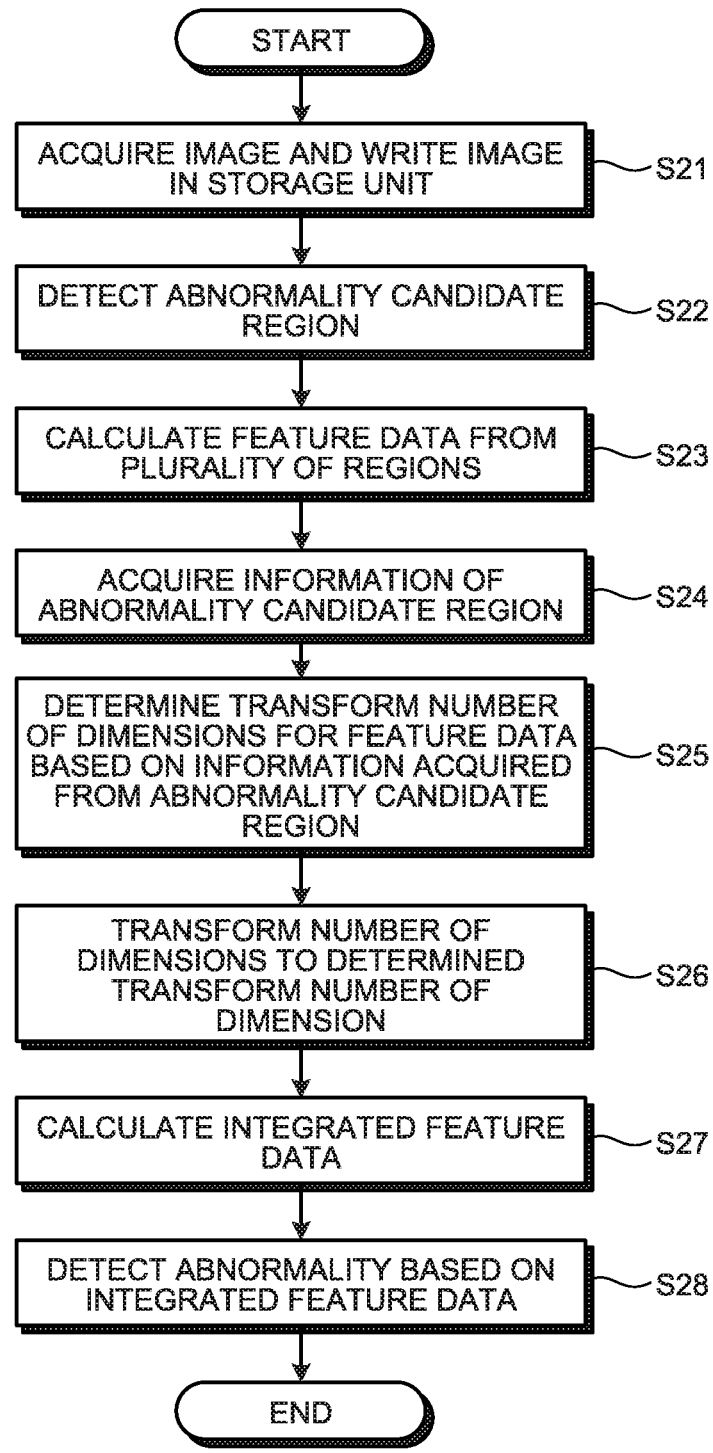
FIG. 10 is a flowchart illustrating an outline of processing executed by the image processing device according to the third embodiment of the present disclosure.

FIG. 10 is a flowchart illustrating an outline of processing performed by the image processing device 11. Processing in steps S21 to S24 and S28 is similar to processing in steps S1 to S4 and S7 in FIG. 4, respectively.

In step S25, the feature data transform dimension number determination unit 641 determines transform number of dimensions for feature data based on information of an abnormality candidate region (step S25).

Subsequently, the integrated feature data calculation unit 13 transforms the number of dimensions to the transform number of dimensions for the feature data determined by the feature data transform dimension number determination unit 641 by a known principal component analysis, the kernel method, or the like (step S26). Note that the transform number of dimensions may be smaller or larger than the number of dimensions for the feature data before transform.

After that, the integrated feature data calculation unit 13 calculates integrated feature data obtained by integrating a plurality of pieces of feature data by using the BoF, Fisher Vector, or the like (step S27). In the third embodiment, the number of dimensions for integrated feature data is predetermined in a manner similar to the first embodiment.

After the detection unit 7 detects an abnormality in step S28, the image processing device 11 finishes a series of the processing.

According to the third embodiment of the present disclosure described above, since an abnormality candidate region is detected and a plurality of kinds of feature data is integrated based on information of the detected abnormality candidate region, the integrated feature data suitable for accurately representing an observation object may be appropriately acquired in a manner similar to the first embodiment.

Additionally, according to the third embodiment, since the transform number of dimensions for feature data is suitably determined in accordance with information of an abnormality candidate region, the integrated feature data according to the abnormality candidate region may be calculated, and erroneous detection and detection failure may be suppressed.

Modified Example 3-1

A second example of feature data transform dimension number determination processing performed by the feature data transform dimension number determination unit 641 will be described as a modified example 3-1 of the present embodiment. The feature data transform dimension number determination unit 641 determines transform number of dimensions for feature data based on clarity at a boundary of an abnormality candidate region. Specifically, when the boundary is clear, the feature data transform dimension number determination unit 641 sets the transform number of dimensions for the feature data to become smaller than that when the boundary is unclear. This is because, when the boundary is clear, it may be considered that a significant difference appears in an abnormal region and a normal region.

Modified Example 3-2

A third example of the feature data transform dimension number determination processing performed by the feature data transform dimension number determination unit 641 will be described as a modified example 3-2 of the present embodiment. The feature data transform dimension number determination unit 641 determines transform number of dimensions for feature data based on an organ kind in an image in which an abnormality candidate region is captured. Specifically, the feature data transform dimension number determination unit 641 sets the transform number of dimensions for feature data of an organ to be examined to become larger than that of an organ not to be examined. Consequently, the organ to be examined may be accurately detected.

Modified Example 3-3

A fourth example of the feature data transform dimension number determination processing performed by the feature data transform dimension number determination unit 641 will be described as a modified example 3-3 of the present embodiment. The feature data transform dimension number determination unit 641 determines transform number of dimensions for feature data based on whether an abnormality candidate region exists in a bubble inner region. Specifically, when the abnormality candidate region exists in the bubble inner region, the feature data transform dimension number determination unit 641 sets the transform number of dimensions for the feature data to become larger than that when of existing in a bubble outer region. This is because, when the abnormality candidate region exists in the bubble inner region, a mucosal region has strong redness and it may be considered that a significant difference hardly appears between an abnormal region and a normal region.

Modified Example 3-4

A fifth example of the feature data transform dimension number determination processing performed by the feature data transform dimension number determination unit 641 will be described as a modified example 3-4 of the present embodiment. The feature data transform dimension number determination unit 641 determines transform number of dimensions for feature data based on whether an abnormality candidate region exists in a dark region. Specifically, when the abnormality candidate region exists in the dark region, the feature data transform dimension number determination unit 641 sets the transform number of dimensions for the feature data to become larger than that in the case of existing in a non-dark region. This is because, when the abnormality candidate region exists in the dark region, it may be considered that a significant difference hardly appears between an abnormal region and a normal region.

Modified Example 3-5

A sixth example of the feature data transform dimension number determination processing performed by the feature data transform dimension number determination unit 641 will be described as a modified example 3-5 of the present embodiment. The feature data transform dimension number determination unit 641 determines transform number of dimensions for feature data based on whether an abnormality candidate region exists in a halation region. Specifically, when the abnormality candidate region exists in the halation region, the feature data transform dimension number determination unit 641 sets the transform number of dimensions for the feature data to become larger than that in the case of existing in a non-halation region. This is because, when the abnormality candidate region exists in the halation region, it may be considered that a significant difference hardly appears between an abnormal region and a normal region.

Modified Example 3-6

A seventh example of the feature data transform dimension number determination processing performed by the feature data transform dimension number determination unit 641 will be described as a modified example 3-6 of the present embodiment. The feature data transform dimension number determination unit 641 determines transform number of dimensions for feature data based on a mucosal color in an image. Specifically, when the mucosal color in the image has strong redness, the feature data transform dimension number determination unit 641 sets the transform number of dimensions for the feature data to become larger than that when the mucosal color has weak redness. This is because, when the mucosal color in the image has the strong redness, it may be considered that a significant difference hardly appears between an abnormal region and a normal region.

Needless to mention, the modified examples 3-1 to 3-6 described above bring effects similar to those of the above-described third embodiment.

Note that the processing of the feature data transform dimension number determination unit 641 described in the modified examples 3-1 to 3-6 may be suitably combined with the processing of the feature data transform dimension number determination unit 641 described in the third embodiment. For example, an average of the number of dimensions determined in respective feature data transform dimension number determination processing may be determined as transform number of dimensions for feature data. Additionally, priority order may be preset for a plurality of feature data transform dimension number determination processing to be combined, and it may be possible to finally determine, as the transform number of dimensions, the number of dimensions obtained by adding, to the number of dimensions determined by each feature data transform dimension number determination processing, a weight in accordance with the priority order.

Other Embodiments

While the modes to implement the present disclosure have been described above, it should be noted that the present disclosure is not be limited only by the above-described first to third embodiments. For example, the parameter control unit may include two or more of the feature data selectors 621, integrated feature data dimension number determination units 631, and feature data transform dimension number determination units 641. In this case, it is possible to combine two or more of the feature data selecting processing, integrated feature data dimension number determination processing, and feature data transform dimension number determination processing.

Furthermore, while the feature data calculation unit 5 sets a circular region based on an extended region obtained by extending an abnormality candidate region in accordance with an expression (1) in the first embodiment, the circular region may also be set based on a reduced region obtained by reducing an abnormality candidate region.

According to the present disclosure, since the abnormality candidate region is detected and the plurality of kinds of feature data is integrated based on the information of the detected abnormality candidate region, the integrated feature data suitable to represent an observation object may be obtained with high accuracy.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a processor comprising hardware, wherein the processor is configured to:
   detect, from an intraluminal image obtained by imaging a lumen of a living body, an abnormality candidate region in which a tissue characteristic of the living body or an in-vivo state satisfies a predetermined condition;
   calculate, from each of a plurality of regions inside the intraluminal image, a plurality of pieces of feature data including different kinds;
   acquire information of the abnormality candidate region;
   estimate an abnormality kind in the abnormality candidate region;
   set, as a calculation parameter, one of:
      number of dimensions for each kind of feature data used to calculate integrated feature data, based on the information of the abnormality candidate region; and
      transform number of dimensions for the feature data, based on the information of the abnormality candidate region;
   calculate the integrated feature data by integrating the plurality of pieces of feature data based on the calculation parameter; and
   detect an abnormality from the intraluminal image by using the integrated feature data.

2. The image processing device according to claim 1, wherein the processor is configured to select feature data to be used when calculating the integrated feature data based on the abnormality kind estimated.

3. The image processing device according to claim 2, wherein the abnormality kind estimated comprises abnormality of a color in the intraluminal image, abnormality of a shape in the intraluminal image, and abnormality of texture in the intraluminal image, and wherein the processor is configured to preferentially select, in accordance with the abnormality kind estimated, feature data corresponding to the abnormality kind estimated over feature data corresponding to other abnormality kinds.

4. The image processing device according to claim 1, wherein the processor is configured to:
estimate the abnormality kind in the abnormality candidate region by a plurality of methods different from each other; and
select feature data to be used when calculating the integrated feature data by combining at least part of estimation results of the abnormality kind by the plurality of methods.

5. The image processing device according to claim 1, wherein the processor is configured to:
estimate, as the abnormality kind, which one of a color, a shape and texture an abnormality exists in; and
determine the number of dimensions,
wherein the number of dimensions when an abnormality exists in the color is set smaller than the number of dimensions when an abnormality exists in the shape and/or the texture.

6. The image processing device according to claim 1, wherein the processor is configured to:
estimate the abnormality kind in the abnormality candidate region based on a plurality of methods different from each other, and
perform at least any one of:
determine the number of dimensions for the integrated feature data by combining at least part of estimation results of the abnormality kind by the plurality of methods; and
determine transform number of dimensions for the feature data.

7. The image processing device according to claim 1, wherein the processor is configured to calculate clarity at a boundary of the abnormality candidate region.

8. The image processing device according to claim 7, wherein the processor is configured to select feature data to be used when calculating the integrated feature data.

9. The image processing device according to claim 8, wherein the processor is configured to:
preferentially select at least one of color feature data and shape feature data when the boundary is clear; and
preferentially select texture feature data when the boundary is unclear.

10. The image processing device according to claim 7, wherein the processor is configured to, set the number of dimensions when the boundary is clear to be smaller than the number of dimensions when the boundary is unclear.

11. The image processing device according to claim 1, wherein the processor is configured to calculate information on a peripheral region of the abnormality candidate region.

12. The image processing device according to claim 11, wherein the processor is configured to select feature data to be used when calculating the integrated feature data based on the information on the peripheral region of the abnormality candidate region.

13. The image processing device according to claim 12, wherein the processor is configured to categorize organs in the intraluminal image into kinds.

14. The image processing device according to claim 13, wherein the processor is configured to:
when the kind of the organ is the stomach or small intestine, preferentially select at least one of color feature data and texture feature data; and
when the kind of the organ is a large intestine, preferentially select shape feature data.

15. The image processing device according to claim 12, wherein the processor is configured to determine whether the abnormality candidate region exists in a bubble inner region.

16. The image processing device according to claim 15, wherein the processor is configured to, when the abnormality candidate region exists in a bubble inner region, preferentially select at least one of shape feature data and texture feature data.

17. The image processing device according to claim 12, wherein the processor is configured to determine at least one of whether the abnormality candidate region exists in a dark region and whether the abnormality candidate region exists in a halation region.

18. The image processing device according to claim 17, wherein the processor is configured to, when the abnormality candidate region exists in a dark region or a halation region, preferentially select at least one of shape feature data and texture feature data.

19. The image processing device according to claim 12, wherein the processor is configured to abnormality calculate a mucosal color in the intraluminal image.

20. The image processing device according to claim 19, wherein the processor is configured to:
preferentially select color feature data when the mucosal color has weak redness; and
preferentially select at least one of shape feature data and the texture feature data when the mucosal color has strong redness.

21. The image processing device according to claim 11, wherein the processor is configured to categorize organs in the intraluminal image into kinds.

22. The image processing device according to claim 21, wherein the processor is configured to, when determining the number of dimensions, set the number of dimensions for an organ to be examined to be larger than the number of dimensions for an organ not to be examined.

23. The image processing device according to claim 11, wherein the processor is configured to determine whether the abnormality candidate region exists in a bubble inner region.

24. The image processing device according to claim 23, wherein the processor is configured to, when determining the number of dimensions, set the number of dimensions when the abnormality candidate region exists in the bubble inner region to be larger than the number of dimensions when the abnormality candidate region exists a bubble outer region.

25. The image processing device according to claim 11, wherein the processor is configured to determine at least one of whether the abnormality candidate region exists in a dark region and whether the abnormality candidate region exists in a halation region.

26. The image processing device according to claim 25, wherein the processor is configured to, when determining the number of dimensions, set the number of dimensions when the abnormality candidate region exists in the dark region or the halation region to be larger than the number of dimensions when the abnormality candidate region exists in a non-dark region or a non-halation region.

27. The image processing device according to claim 11, wherein the processor is configured to calculate a mucosal color in the intraluminal image.

28. The image processing device according to claim 27, wherein the processor is configured to, when determining the number of dimensions, setting the number of dimensions when the mucosal color has strong redness to be larger than number of dimensions when the mucosal color has weak redness.

29. An image processing method comprising:
detecting, from an intraluminal image obtained by imaging a lumen of a living body, an abnormality candidate region in which a tissue characteristic of the living body or an in-vivo state satisfies a predetermined condition;
calculating, from each of a plurality of regions inside the intraluminal image, a plurality of pieces of feature data including different kinds;
acquiring information of the abnormality candidate region;
estimating an abnormality kind in the abnormality candidate region;
setting, as a calculation parameter, one of:
number of dimensions for each kind of feature data used to calculate integrated feature data, based on the information of the abnormality candidate region; and
transform number of dimensions for the feature data, based on the information of the abnormality candidate region;
calculating the integrated feature data by integrating the plurality of pieces of feature data based on the calculation parameter; and
detecting an abnormality from the intraluminal image by using the integrated feature data.

30. A non-transitory computer-readable recording medium with an executable program stored thereon, wherein the program causing a processor to execute:
detecting, from an intraluminal image obtained by imaging a lumen of a living body, an abnormality candidate region in which a tissue characteristic of the living body or an in-vivo state satisfies a predetermined condition;
calculating, from each of a plurality of regions inside the intraluminal image, a plurality of pieces of feature data including different kinds;
acquiring information of the abnormality candidate region;
estimating an abnormality kind in the abnormality candidate region;
setting, as a calculation parameter, one of:
number of dimensions for each kind of feature data used to calculate integrated feature data, based on the information of the abnormality candidate region; and
transform number of dimensions for the feature data, based on the information of the abnormality candidate region;
calculating the integrated feature data by integrating the plurality of pieces of feature data based on the calculation parameter; and
detecting an abnormality from the intraluminal image by using the integrated feature data.

* * * * *